United States Patent [19]
O'Young et al.

[11] Patent Number: 5,227,569
[45] Date of Patent: Jul. 13, 1993

[54] SKELETAL ISOMERIZATION OF N-BUTYLENES TO ISOBUTYLENE ON BORON-BETA ZEOLITES

[75] Inventors: Chi-Lin O'Young, Poughkeepsie; John Hazen, Cragsmoor; Daniel G. Casey, Poughkeepsie, all of N.Y.

[73] Assignee: Texaco Inc., White Plains, N.Y.

[21] Appl. No.: 747,054

[22] Filed: Aug. 19, 1991

[51] Int. Cl.$^5$ ............................................... C07C 5/22
[52] U.S. Cl. .................................................... 585/671
[58] Field of Search ......................................... 585/671

[56] References Cited

U.S. PATENT DOCUMENTS 4,503,282  3/1985  Sikkenga ............................. 585/671

Primary Examiner—Patrick P. Garvin
Assistant Examiner—Brent M. Peebles
Attorney, Agent, or Firm—James J. O'Loughlin; Vincent A. Mallare

[57] ABSTRACT

Normal olefins such as n-butenes can be converted to iso olefins such as isobutylene by skeletal isomerization over catalysts of boron-beta zeolites having pore sizes of at least about 5 Angstroms and containing boron in the framework structure thereof. The boron-beta zeolites have sufficient acidity to catalyze the skeletal isomerization of normal olefins to iso-olefins. The catalysts can be used to produce iso-olefins for reaction with alcohols in integrated processes to produce alkyl tertiary alkyl ethers such as MTBE.

11 Claims, 4 Drawing Sheets

SKELETAL ISOMERIZATION OF N-BUTYLENES TO ISOBUTYLENE ON BORON-BETA ZEOLITES

BACKGROUND OF THE INVENTION

This invention relates to olefin isomerization. In one of its more specific aspects, this invention relates to selective isomerization of olefins.

More particularly, the present invention relates to a process for the preparation of useful hydrocarbons by catalytic conversion of n-butylenes.

MTBE (methyl tertiary butyl ether) is an effective octane booster. It is made from isobutylene and methanol. The present sources of isobutylene for MTBE production are mainly from by products of steam, catalytic cracker, and propylene oxide production. However, these supplies are limited. Other possible sources are by isomerization of n-butenes taken from steam or catalytic crackers and by dehydrogenation of isobutane taken from field butanes or produced by isomerization of n-butane.

Olefin isomerization processes can be directed towards either skeletal isomerization or double bond isomerization. Skeletal isomerization is concerned with reorientation of the molecular structure in respect to the formation or elimination of side chains. Double bond isomerization is concerned with relocation of the double bond between carbon atoms while maintaining the backbone of the carbon structure. Most isomerization processes give rise only to double bond isomerization.

The minimum Brönsted Acid strengths (and equivalents in $H_2SO_4$) required for various acid-catalyzed conversions of hydrocarbons are indicated in the table below.

Minimum Brönsted Acid Strength Required For The Acid-Catalyzed Conversions of Hydrocarbons

| $H_R$ Required | Reaction Type |
|---|---|
| < +0.8<br>1.2 wt % $H_2SO_4$ | Cis-trans Isomerization of Olefins |
| < −6.6<br>48 wt % $H_2SO_4$ | Double-bond Migration |
| < −11.6<br>68 wt % $H_2SO_4$ | Skeletal Isomerization |
| < −16.0<br>88 wt % $H_2SO_4$ | Cracking of Alkanes |

It is frequently necessary to convert olefins into other olefins having a different skeletal arrangement. For example, normal butenes are converted into isobutene for polymerization, alkylation, disproportionation, etc. Similarly, normal amylenes must be converted to isoamylenes prior to dehydrogenation to isoprene.

While a number of catalytic materials possess some activity for such a conversion, not all possess sufficient selectivity to be economical. Because the feeds are generally the relatively reactive olefins, many catalysts cause undesirable side reactions such as polymerization or cracking. Consequently, there is a continuing interest in the development of new skeletal isomerization catalysts and processes for isomerizing alkanes as well as alkenes to improve efficiencies and to give optimum results for various industrial requirements. A comprehensive review is provided by V. R. Choudhary in "Catalytic Isomerization of n-butene to Isobutene," *Chem. Ind.* Dev, pp. 32–41 (1974).

It is generally known that n-paraffins with, for example, 4 to 7 carbon atoms can be converted to the corresponding isomeric paraffins by using suitable acid catalysts in the temperature range of from 100° to 250° C. Examples of this process are the numerous isomerization processes used in the petrochemical and mineral oil industries for increasing the octane number of light, paraffinic mineral oil fractions. Furthermore, it is known that, in contrast to this, olefins of the same number of carbon atoms cannot be converted to the corresponding isoolefins except under difficult conditions, for example at very high temperatures and with poor yield. The attempts hitherto described in the literature for the direct isomerization of the skeleton of e.g. n-butene to give isobutene or e.g. of n-pentene to give isopentenes over catalysts arranged in a fixed bed are characterized by only initially high yields and selectivities, which diminish and deteriorate considerably after a short period of operation, often after only a few hours. The deterioration in the yields and selectivities is generally attributed to the loss of actively effective catalyst surface or to the loss of active centers. In addition to this, high coking rates, formation of oligomers and cracking reactions are observed.

As is known, butylenes or butenes exist in four isomers: butene-1, cis-butene-2, its stereo-isomer transbutene-2, and isobutene. Conversions between the butenes-2 are known as geometric isomerization, whereas those between butene-1 and the butenes-2 are known variously as position isomerization, double-bond migration, or hydrogen-shift isomerization. These three isomers are not branched and are known collectively as normal or n-butenes. Conversion of the n-butenes to isobutene, which is a branched isomer, is widely known as skeletal isomerization. The same general terminology is used when discussing skeletal isomerization of other n-alkanes and olefins, as well as paraffinic compounds such as n-alkenes.

Isobutene has become more and more important recently as one of the main raw materials used in the production of methyl tert-butyl ether (MTBE), an environmentally-approved octane booster to which more and more refiners are turning as metallic additives are phased out of gasoline production. However, processes for the skeletal isomerization of olefins e.g., to produce isobutene, are relatively non-selective, inefficient, and short-lived because of the unsaturated nature of these compounds. On the other hand, positional and skeletal isomerization of paraffins and alkyl aromatics are fairly well established processes, in general utilizing catalysts typically comprising metallic components and acidic components, under substantial hydrogen pressure. Since paraffins and aromatics are stable compounds, these processes are quite successful. The heavier the compounds, in fact, the less severe the operating requirements. Olefins, however, are relatively unstable compounds. Under hydrogen pressure, they are readily saturated to the paraffinic state.

Furthermore, in the presence of acidity, olefins can polymerize, crack and/or transfer hydrogen. Extensive polymerization would result in poor yields, and short operating cycles. Similarly, cracking would reduce yield. Hydrogen transfer would result in saturated and highly unsaturated compounds, the latter being the common precursors for gum and coke. Any theoretical one step process for producing skeletal isomers of, for example, n-butenes, would have to be concerned with the unwanted production of butanes and the reverse problem of production of butadienes. In addition to these problems, it is well known that skeletal isomerization becomes more difficult as hydrocarbons get lighter.

Skeletal isomerization of olefins is known to be accomplished by contacting unbranched or lightly branched olefins with acidic catalysts at elevated temperatures. The process is generally applicable to the isomerization of olefins having from 4 to about 20 carbon atoms and is especially applicable to olefins having from 4 to about 10 carbon atoms per molecule. The process may be used to form isobutene from normal butenes, methyl pentenes and dimethyl butenes from normal hexenes, and so forth.

Thus, among the objects of this invention are improved processes for the skeletal isomerization of n-butylene and olefins, especially for the isomerization of n-butylene to form isobutylene.

A more specific object is an easily prepared, stable, active multifunctional isomerization catalyst and processes for the skeletal isomerization of hydrocarbon species including olefins.

Other objects and advantages of the invention will be apparent from the following description, including the drawing and the appended claims.

DISCLOSURE STATEMENT

Known skeletal isomerization catalysts include aluminas and halogenated aluminas, particularly F- or Cl-promoted aluminas. Supports employed in such catalysts are either alumina or predominantly alumina due mainly to the high acidity of alumina. See Choudhary, V. R., "Fluorine Promoted Catalysts: Activity and Surface Properties", Ind. *Eng. Chem., Prod. Res. Dev.*, 16(1), pp. 12–22 (1977) and U.S. Pat. No. 4,400,574. Numerous catalysts employ a metal or metal oxide in conjunction with a halide-treated metal oxide. For example, U.S. Pat. No. 4,410,753 discloses isomerization catalysts comprising $Bi_2O_3$ on fluorided alumina and U.S. Pat. No. 4,433,191 discloses skeletal isomerization catalysts comprising a Group VIII metal on halided alumina. Many of the catalysts including halide-treated components require periodic addition of halide materials to maintain catalyst activity; for example, see U.S. Pat. Nos. 3,558,734 and 3,730,958. An average yield for isobutene of 25 weight percent (within an observed range of 17 to 33 percent) is typically reported when using halided catalysts, based upon a review of various patents cited in this disclosure.

Amoco has patents disclosing that n-butane can be converted to isobutylene in one step, i.e. by dehydrogenation n-butenes to isobutylene. For example, see U.S. Pat. Nos. 4,435,311 and 4,433,190 and other co-assigned patents referred to therein. The catalysts employed contain an AMS-1B borosilicate (also called [B]-ZSM-5 or Boralite C) and a noble metal such as platinum. This process is economically quite attractive because two catalytic reactions, dehydrogenation and isomerization, are carried out in one step by a bifunctional catalyst. Such reactions could potentially solve the surplus n-butane problem and produce high-octane MTBE.

Various techniques have been employed to improve the effectiveness of materials such as alumina and silica as structural isomerization catalysts. For example, U.S. Pat. No. 3,558,733 discloses methods for activating alumina catalysts with steam, U.S. Pat. No. 4,405,500 discloses catalysts prepared by controlled deposition of silica on alumina and U.S. Pat. No. 4,587,375 discloses a steam-activated silicalite catalyst. In addition, various metal oxides have been used to improve the effectiveness of catalysts based upon alumina, silica or the like.

Zeolitic materials, especially in their hydrogen forms, are known to behave as strong acids. Due to their narrow yet regular pore size they are quite effective in catalyzing olefin polymerization. Unfortunately the pores are soon plugged due to deposition of polymeric materials and frequent catalyst regeneration is necessary to maintain activity.

Natural and synthetic zeolites have been widely used as catalysts, catalyst supports and the like for processes of hydrocarbon conversion. Additional components such as metals, in the elemental, oxide or cation form are often included in such catalysts. For example, U.S. Pat. No. 3,849,340 discloses a "catalytic composite" comprising a mordenite having a silica/alumina ratio of at least 40:1 and a metal component selected from copper, silver and zirconium. U.S. Pat. No. 4,608,355 also discloses hydrocarbon conversion catalysts formed by compositing a clay matrixing material with a zeolite containing cations of Group IB metals such as silver. The presence of such cations is said to give the zeolite improved resistance to high sintering temperatures encountered in catalyst fabrication. The metal loaded zeolites can be mixed with a porous matrix and calcined prior to use. These catalysts are stated to be useful in processes such as catalytic cracking, the conversion of oxygenates to hydrocarbons, and the like.

U.S. Pat. No. 4,433,190, assigned to Standard Oil Co. (Indiana), discloses processes for the conversion of alkanes such as n-butane to dehydrogenated and isomerized products by contact with catalysts containing AMS-1B crystalline borosilicates containing ions or molecules of catalytically active elements such as noble metals. These borosilicates have topological structures similar to those of ZSM-5 zeolites. The products can include isobutylene, n-butene and isobutane.

U.S. Pat. No. 4,503,292, also assigned to Standard Oil Co. (Indiana), discloses processes for converting n-alkenes to isoalkenes using catalysts containing AMS-1B borosilicate as at least 50 weight percent of the catalyst composition. The borosilicate can be cation-exchanged with hydrogen or metals selected from Groups IB, IIA, IIB, IIIA, VIB and VIII as well as manganese, vanadium, chromium, uranium and rare earth elements. The borosilicate can also be impregnated with metals of Groups IB, IIA, IIB, IIIA, IVB, VB, VIB, VIIB and VIII and rare earth elements.

U.S. Pat. No. 4,435,311, also assigned to Standard Oil Co. (Indiana) discloses a process for regenerating catalysts containing AMS-1B borosilicates and noble metals by contacting them with water. The process can be carried out during the process of conversion of feedstocks such as alkanes and alkenes to isomerized products such as isoolefins. Similar conversion processes employing catalysts containing such borosilicates are disclosed in U.S. Pat. Nos. 4,777,310; 4,503,282; 4,499,325 and 4,499,326, all assigned to Standard Oil or Amoco Corp.

U.S. Pat. No. 4,656,016 discloses silicalites and similar silica-based molecular sieves which contain boron or other amphoteric elements in quantities sufficient to adjust the acidity of the sieves, plus catalytic metals such as copper, nickel, cobalt, tungsten, platinum and palladium. The reactions which can be catalyzed by such materials are listed in column 4, including hydrogenation/dehydrogenation of hydrocarbons and conversion of olefins into "high-octane fuel products."

Columns 9 and 10 contain descriptions of silicalites containing boron in the framework structure, referred to as "Boralites A, B, C and D." These species are identified as having structures resembling those of zeolites NU-1, Beta, ZSM-5 and ZSM-11, respectively, by Taramasso et al in "Molecular Sieve Borosilicates", in *Proceedings, 5th Intl. Conference on Zeolites*, pp. 40–48, Naples, 1980 (L. V. Rees, ed.) - (Heyden, London, 1980).

U.S. patent application Ser. No. D# 79,413 discloses that normal olefins such as n-butenes and normal alkanes such as n-butane can be converted to branched olefin species such as isobutylene by skeletal isomerization over catalysts preferably containing metals selected from Groups IB, IIB, IIIB, IVB, VB, VIB, VIIB, VIII and the rare earth elements which are deposited upon borosilicate zeolites having pore sizes of at least about 5 Angstroms and containing boron in the framework structure thereof. The borosilicates have sufficient acidity to catalyze the skeletal isomerization of both normal alkanes and normal olefins. The borosilicate zeolites may be synthesized using ammonium or tetra-alkyl ammonium ions as organic templates.

U.S. patent application Ser. No. (D#79,415) discloses that normal olefins such as n-butenes can be converted to iso-olefins such as isobutylene by skeletal isomerization over catalysts of boron-beta zeolites having pore sizes of at least about 5 Angstroms and containing boron in the framework structure thereof. The boron-beta zeolites have sufficient acidity to catalyze the skeletal isomerization of normal olefins.

SUMMARY OF THE INVENTION

In accordance with the present invention, a multifunctional catalyst composition for the skeletal isomerization of normal olefins comprises at least one borosilicate zeolite. A binder of an inorganic oxide such as alumina, silica, silica-alumina, clays and combinations thereof can optionally be employed with the borosilicate zeolite.

The borosilicate zeolites are prepared by a process comprising the steps of:

(a) preparing a basic reaction mixture of at least about Ph 9 comprising in suitable proportions a silicon source, a boron source and an organic template;

(b) heating the reaction mixture in a closed vessel under conditions of temperature, autogenous pressure and time effective to produce a crystalline product containing boron oxides in the framework structure thereof;

(c) recovering the crystalline product; and (d) calcining the crystalline product under conditions effective to remove the organic template without substantial damage to the framework structure of the crystalline product, whereby the n-olefins are converted to olefins.

To achieve the calcining effect which removes the organic template without damaging the crystal structure, the product is preferably subjected to at least one period of calcining in an inert atmosphere such as nitrogen, followed by at least one period of calcining in an atmosphere containing oxygen. The zeolites can be converted to the hydrogen form by cation-exchanging with ammonium ion to remove sodium, then calcining to remove ammonia. The exchange step can be eliminated if certain organic templates containing tetraalkyl ammonium ions are used, as calcining drives off ammonia and organic residues, with hydrogen ions remaining.

Such boron-substituted zeolites, optionally, in combination with dehydrogenation metals as described below, can be employed in catalysts having activity for the structural isomerization or dehydroisomerization of normal alkanes such as butane, the dehydrogenation of isoalkanes such as isobutane and the structural isomerization of normal alkenes such as n-butenes. Such catalysts can be used to treat mixed feedstreams containing such species to products rich in isoolefins such as isobutene. Byproducts including such species can be recycled to the reactor for additional passes so as to maximize the conversion to the desired product(s). The isoolefins are desired reactants in the production of alkyl tertiary-alkyl ethers such as methyl tertiary-butyl ether, and processes for the production of such ethers can be integrated with the hydrocarbon conversion processes of the present invention.

Further in accordance with the invention, processes chain olefins by skeletal isomerization comprise steps of contacting the olefins and/or alkanes (which can be at least about 20 weight percent of a mixed feedstock) under skeletal isomerization conditions with a multifunctional catalyst of the invention. The catalyst can include a boron-substituted zeolite containing sufficient boron to provide sufficient acidity in the zeolite to catalyze the skeletal isomerization of normal alkenes, preferably without substantial cracking. Optionally, the catalyst includes at least one dehydrogenation metal selected from the group consisting of Groups IB, IIB, IIIB, IVB, VB, VIB, VIIB and VIII of the Periodic Table, plus rare earth metals. Preferably the metal is a noble metal selected from platinum, palladium, iridium, rhodium and ruthenium. Preferred embodiments include combinations of metals which are more effective in catalysts to be used at relatively high temperatures, for example noble metals in combination with rhenium. The boron-substituted zeolite should have a pore size of at least about 5 Angstroms, and preferably is characterized by a topological structure selected from the group consisting of ZSM-5, ZSM-11, NU-1, Beta, Omega (MAZ), FAU and mordenite (MOR) zeolites.

Operable conditions include temperatures in the range of about 300° to 650° C., preferably 450° to 550° C.; pressures ranging from about 0.5 to about 40 psi and weight hourly space velocities (WHSV) ranging from about 0.1 to about 20 weight of olefin/weight of catalyst per hour. The normal olefins and/or alkanes can have from 4 to about 12 carbon atoms, preferably about 4 to 6, and preferably include n-butene and/or n-butane.

In a preferred embodiment, the normal olefins are contained in a feedstock which also contains branched o olefins, and the product of the skeletal isomerization step is reacted with an alkanol having from 1 to about 5 carbon atoms (such as methanol or ethanol) under catalytic conditions effective to produce at least one methyl tertiary-alkyl ether, such as methyl tertiary-butyl ether, or ethyl tertiary-butyl ether.

DETAILED DESCRIPTION OF THE INVENTION

Figure 1:
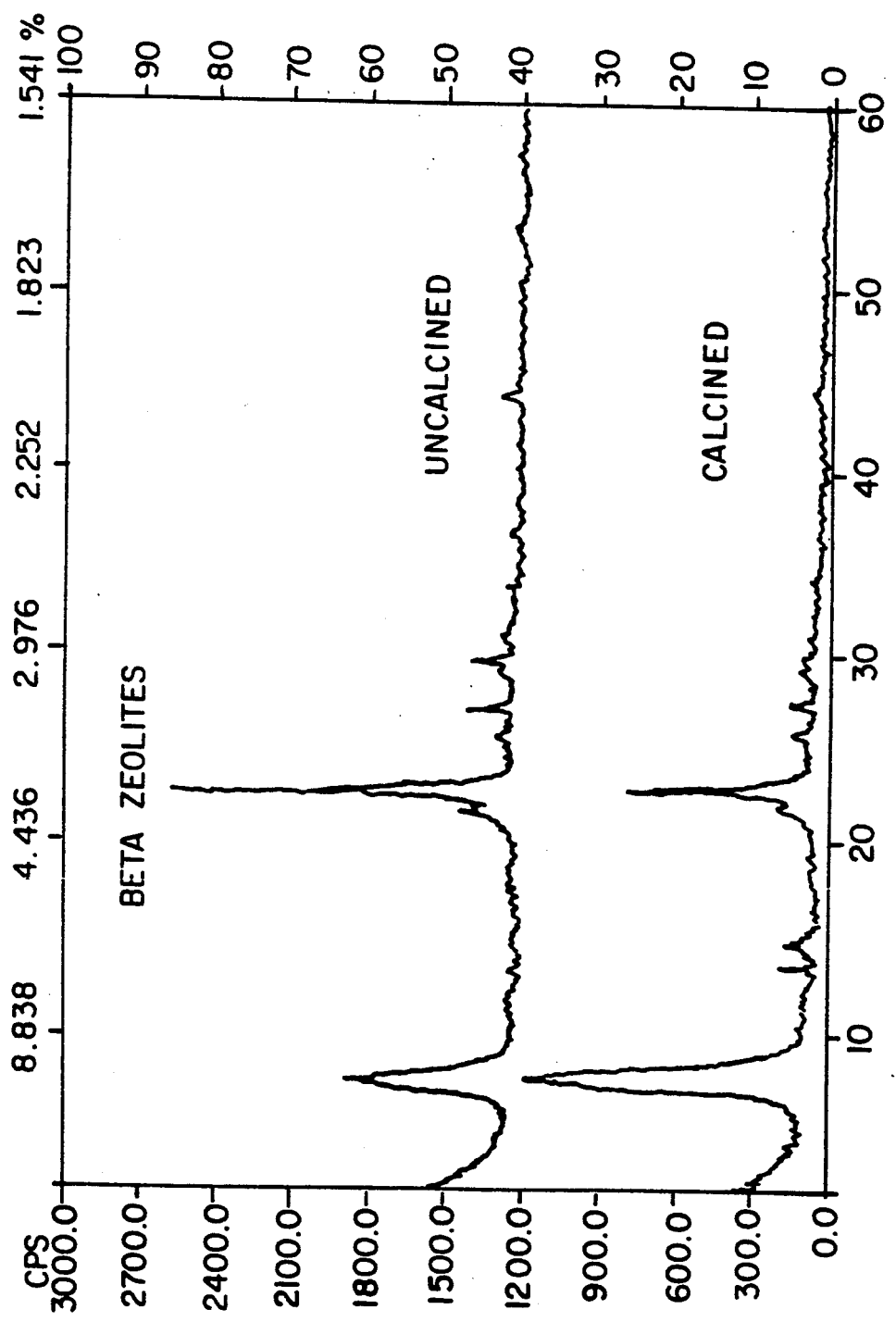
FIG. 1 is an X-ray diffraction spectrum of uncalcined and calcined boron-beta zeolite.

As discussed above, the skeletal isomerization catalysts of the present invention employ medium to large pore zeolites containing boron in the framework structures. For the purposes of this application, a medium pore zeolite is one with a channel of at least about size greater than 5 Å, while the large pore channels are greater than 5.6 Å; the zeolite is preferably one with channels of 7.0 to 7.4 Å. Typical materials of this structural type would include: mordenite, faujasite, X, Y, and L zeolites, mazzite, ZSM-4, ZSM-5, ZSM-11, zeolite omega, zeolite beta, ZSM-20, NU-1 and gmelinite.

The medium to large pore boron zeolites useful in the present invention are preferably selected from the groups of topologically-related zeolite structures listed below in Table I and published in the *Atlas of Zeolite Structure Types* by Meier and Olson, published on behalf of the Structure Commission of the International Zeolite Association by Butterworths & Co. Ltd. (London, 1988), following rules set up by a Commission of Zeolite Nomenclature of the International Union of Pure and Applied Chemistry.

TABLE I

| FAU | MOR | MAZ | * |
|---|---|---|---|
| Faujasite | Mordenite | Mazzite | NU-1 |
| X (Linde) | Ptilolite | Omega | Beta |
| Y (Linde) | Zeolon | | |
| N-Y | | | |
| ZSM-20 | | | |

* No code assigned to this group.

Zeolite ZSM-20 is described in U.S. Pat. Nos. 3,972,983 and 4,021,331 and zeolite beta in U.S. Pat. No. 3,303,069 and Re. 28,341; zeolite L is disclosed in U.S. Pat. No. 3,216,789, zeolite omega is disclosed in U.S. Pat. No. 4,241,036, ZSM-4 is disclosed in U.S. Pat. No. 3,578,723, zeolite X is disclosed in U.S. Pat. No. 2,882,244 and zeolite Y is disclosed in U.S. Pat. No. 3,130,007; reference is made to these patents for details of these zeolites, their preparation and properties. Many suitable forms of these zeolites can be employed, including variations in silica/alumina ratio, silicon/boron ratio, cell size and the like.

Synthesis of Boron Substituted Zeolites

NU-1, Beta, ZSM-5, and ZSM-11 zeolites can be prepared by the same family of organic templates, tetraalkylammonium ions. The formation of each phase depends on the type of template used, on the reaction conditions, and on the gel composition. Table II below shows the types of zeolites and boron-zeolites which can be produced with tetraalkylammonium templates. ZSM-5 can be synthesized in the presence of TPA and TEA ions, while ZSM-11 can be synthesized in the presence of TBA ion. Both of these pentasil structures have frameworks containing two intersecting channel systems with 10-ring openings. For ZSM-11 the two channel systems are straight, but for ZSM-5 one channel is straight and the other one is zigzag or sinusoidal. See, e.g. Coudurier et al, *J. Catalysis,* Vol. 108, p. 1 (1987). [B]-ZSM-11 zeolites are presently preferred since they have outperformed [B]-ZSM-5, possibly at least in part because of the more open pore structure.

NU-1 and Beta zeolites can be synthesized in the presence of TMA and TEA ions, respectively. The structure of Beta has been solved recently. It has a three dimensional interconnected tunnel system with 12-ring openings. The structure of NU-1 is not clear, but it seems to have a dual pore system with 10-rings and 8-rings based upon adsorption results reported by Dewing et al. in *Catal. Rev. Sci. Eng.,* Vol. 27, pp. 461 (1985).

TABLE II

Synthesis of Zeolites in the Presence of Tetraalkylammonium Ions.

| Template | (Al, Si) zeolite | (B, Si) zeolite |
|---|---|---|
| TMA | NU-1 | Boralite A/[B]-NU-1 |
| TEA | Beta and ZSM-5 | Boralite B/[B]-Beta and Boralite C/[B]-ZSM-5 |
| TPA | ZSM-5 | Boralite C/[B]-ZSM-5 |
| TBA | ZSM-11 | Boralite D/[B]-ZSM-11 |

TMA = tetramethylammonium ion
TEA = Tetraethylammonium ion
TPA = tetrapropylammonium ion
TBA = Tetrabutylammonium ion Also preferred are zeolites with three dimensional pore structures such as the various forms of zeolite Y, since greater access to the reactants is offered. Zeolites characterized by the structure of zeolite Y are also preferred because they have been employed effectively in the examples herein.

When the zeolites are prepared in the presence of organic cations they are initially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite but these cations to favor the formation of the desired crystal structures.

In commercial practice, the zeolite crystallites would be bound together within a matrix comprising alumina, silica-alumina, clay or admixtures thereof. Normally, the finished catalyst would contain at least 10 up to about 85 weight percent of such a binder or matrix. The alumina which is used for the matrix material for the catalyst system of the present invention can be any suitable grade of crystalline or amorphous alumina which is substantially inert. Since the boron zeolites employed have moderate acidity, acidic aluminas should be avoided. The alumina matrix should have a specific surface area of at least about 50 m²/g, preferably in the range of from about 50 to about 500 m²/g, and most preferably from about 100 to about 350 m²/g.

Silica-alumina materials which can be used as binders can be prepared in the same manner as amorphous silica-alumina catalysts, e.g., by adding the zeolite component to a silica-alumina slurry, spray drying, washing the product and drying. Optionally, a clay diluent can be present in the silica-alumina slurry. Such matrixes can be prepared by admixing colloidal alumina (boehmite) and colloidal silica, allowing the matrix properties to vary over a wide range from catalytically inert to active. The activity, thermal stability, surface area and pore distribution of the matrix can be controlled by varying the amounts and particle size distributions of the respective colloids. Further guidance for the preparation of zeolite catalysts containing high porosity matrixes such as silica-alumina can be found in the section by Magee and Blazek on "Zeolite Cracking Catalysts" in ACS Monograph 171, *Zeolite Chemistry and Catalysts* (J. Rabo, Ed.; Am. Chem. Soc., Wash, D.C. 1976).

The zeolite can also be composited with a porous clay matrix material which has suitable binding properties and is resistant to the temperature and other conditions employed in the process. The composite is then calcined to confer the required physical strength. Naturally occurring clays can be composite with the zeolite and these clays can be used in the raw state as originally mined or initially subjected to calcination, acid treatment, chemical modification or purification.

Examples of suitable clays which can be used include the bentonite and kaolin families. Bentonites are mixtures of clays, mainly montmorillonites, which may also contain kaolinite clays. The Wyoming bentonites and montmorillonites are preferred because of their relatively high purity. Kaolin clays include, for example, the Dixie, McNamee-Georgia and Florida clays and others in which the main mineral constituent is halloysite, kaolinite, dickite, nacrite or anauxite. Other clays may also be found to be suitable for use in the present process.

The amount of clay or other matrix material relative to zeolite in the composite will determine, to a certain extent, the physical strength of the final catalyst, especially its attrition resistance and crushing strength. The mechanical properties of the catalyst can therefore be modified by appropriate choice of clay/zeolite ratio, with greater amounts of clay generally conferring better mechanical properties. On the other hand, larger amounts of clay mean that less of the zeolite with its desired, attendant properties will be available to participate in the eventual reaction. A balance will therefore be struck, in most cases, between activity and mechanical properties. Normally, the amount of zeolite will not exceed 50 percent by weight of the composite and in most cases it will not exceed 40 percent by weight and may be lower, e.g. 25 percent by weight or even 15 percent by weight.

The zeolite may conveniently be composited with the clay or other matrix materials by forming an aqueous slurry of the zeolite or zeolites containing the Group IB, VIII or other metal with the clay, spray drying the slurry to form microspheres and then calcining. The zeolite may be in the form of a gel. If the catalyst is to include more than one zeolite, the zeolite may form a cogel with themselves. If one of the zeolites in the zeolite combination is capable of being produced by treatment of a clay, the zeolite may be composited with the clay slurry and the slurry spray dried to form solid zeolite/clay microspheres which are then calcined to confer the desired strength. The clay in the composite may then be converted to the zeolite in the conventional way, e.g. by treatment with sodium hydroxide and heating, followed by ion-exchange, if desired. The mixing and homogenizing steps which may be used in the preparation of the zeolite-matrix mixtures are conventional and need not be described; the spray drying may also be carried out in the conventional manner.

Spent catalysts can be regenerated by heating in a similar oxygen-containing gas, such as air, at temperatures ranging from about 200° C. to about 700° C. This process is significantly simpler than that required for halided metal oxide catalysts, in which a separate step of replacing the halide component must be employed.

The skeletal isomerization processes of this invention are carried out by contacting the feed with the catalyst, using any suitable contacting techniques, at temperatures at which skeletal isomerization of the feed of olefins occurs. The feed is preferably maintained in the vapor phase during contacting. The reactor temperature is preferably in the range of about 300° to about 650° C., more preferably about 450° to about 550° C. The weight hourly space velocity (WHSV) is not narrowly critical but will generally be within the range of about 0.1 to about 20 $hr^{-1}$, preferably from about 1 to about 10 $hr^{-1}$. Any convenient pressure can be used, with the lowest practical pressure preferred in order to minimize side reactions such as polymerization. Preferred pressures are within the range of about 0.2 to about 500 psi, more preferably about 1 to about 30 psi.

The isomerization feedstock contains at least one alkene. Alkenes having 7 or more carbon atoms are generally more likely to crack into light gases than to undergo skeletal isomerization. The alkenes may have terminal or internal double bonds. Butene feedstocks may contain 1-butene, 2-butene or mixtures thereof. Examples of other normal alkenes which are useful feedstocks are 1- and 2-pentenes; 1-, 2- and 3-hexenes; 1-, 2-, and 3-heptenes; and 1-, 2-, 3-, and 4-octenes.

Particular feedstocks contemplated for use in the present process are fractions containing butenes, e.g., n-butenes. Isobutene present in such fractions is commonly converted by catalytic reaction with methanol to produce methyl tertiary-butyl ether ("MTBE"). MTBE is separated by distillation, leaving a residual $C_4$ cut. Isobutene present in such fractions may also be oligomerized to produce oligomers which are then separated, again leaving a residual $C_4$ cut. In either MTBE production or oligomerization, a mixture of n-butenes and isobutene remains in the residual material. It is desirable to produce additional isobutene from the residual material and return the isobutene for further conversion by the reactions mentioned above.

The isomerization feed stream can contain inert gaseous diluents (e.g. paraffins, $N_2$, steam, etc.). The diluent may be present in any desired proportion, e.g., up to about 80 weight percent of the feed stream. Hydrogen can be present in the feed stream in addition to such diluents, and with or without steam can have beneficial effects on the product yield and selectivity as illustrated in Examples 76 to 78.

Selection of isomerization conditions is dependent on the olefins to be isomerized. In general, lower temperatures are used for feeds containing larger olefin molecules. Depending on the specific skeletal isomerization catalysts chosen to carry out the steps of the invention, any suitable reaction technique can be utilized, such as fixed bed reaction, fluidized bed reaction, liquid phase batch and continuous operations, and the like. Conventional methods can be used to separate the materials present in the reaction effluent, including fractionation, crystallization, adsorption, and the like. Fractionation is generally preferred. Saturated materials which accumulate in the system can easily be removed by suitable techniques well known in the art.

In one aspect of the process according to the invention, the conversion of n-alkenes into isoalkenes, preferably n-butenes into isobutene, almost up to the establishment of thermodynamic equilibrium is achieved. This equilibrium, between 400° to 500° C., is about 36 to 40 percent by weight in the case in which the pure system of the n-butenes and isobutene is considered. This equilibrium is frequently not achieved in the case of a single contact of the mixture to be employed according to the invention with the catalyst to be employed during the invention. However, in a particular variant of the process, the product stream leaving the catalyst bed can be divided up, and only one part is directly conveyed to the working-up process, while the other part is again conducted over the catalyst bed. This division of the product stream for recycling can vary within wide limits, for example between the proportions 1:9 to 9:1 of worked-up or recycled material. In this process, a high recycling rate implies a smaller throughput, relative to a constant catalyst charge and constant remaining reaction conditions, but brings a desired shift of the spectrum of components in favor of the isoalkene, e.g. of the isobutene, almost to the thermodynamic equilibrium. On the other hand, a lower recycling rate implies a higher throughput but a poorer approach to the thermodynamic equilibrium. A decision concerning the amount of the recycling rate depends, other process parameters being constant, above all on the composition of the starting hydrocarbon mixture which is available. However, with the catalysts according to the invention, the process can, in general, be operated without a high recycling rate. This can be optimized by simple preliminary experiments.

EXAMPLES

The invention is further illustrated by reference to the following non-limiting examples.

EXAMPLE I

Synthesis of [B]-ZSM-11 Zeolites

A 25 gram quantity of Ludox AS40 (DuPont, 40% $SiO_2$) was added slowly with vigorously stirring to a mixture of solution which contained 2.07 g of $H_3BO_3$, 52.89 g of 55% tetra-n-butylammonium hydroxide (TBAOH) solution, and 189 ml of water. The addition of Ludox gave a curdy, gelatinous, milky slurry. The molar composition of the gel was:

3.36((TBA)$_2$O),1.0($B_2O_3$),10($SiO_2$),680($H_2O$) The solution had a Ph of 13.0. The mixture was transferred to a Teflon liner and sealed in a steel autoclave. The autoclave was kept in an oven at 165° C. for 7 days. After that it was cooled and its contents were filtered. The recovered white crystalline material was washed with copious amounts of water and was dried at 110° C. for 16 h. The dried sample was calcined at 592° C. under nitrogen for 4 hours and then under air for another 2 hours to remove the organic template. The yield was 7.12 g and the sample contained 44.2% Si and 0.24% B. Thus, the approximate weight ratio of silicon to boron (Si/B) was 71.

EXAMPLE II

Synthesis og Boron-Beta Zeolite 50 g of Ludox AS40 (DuPont, 40% $SiO_2$) was added slowly with vigorously stirring to a mixture of solution which contained 0.97 g of $H_2HO_2$, 25.22 g of 40% tetra-n-ethylammonium hydroxide (TEAOH) solution, and 244 ml of water. The addition of Ludox gave a curdy, gelatinous, molky solution. The molar composition of the gel was:

15.0 (TEA)$_2$O, 1.0 ($E_2O_3$), 30 ($SiO_2$), 1800 ($H_2O$).

Figure 2A:
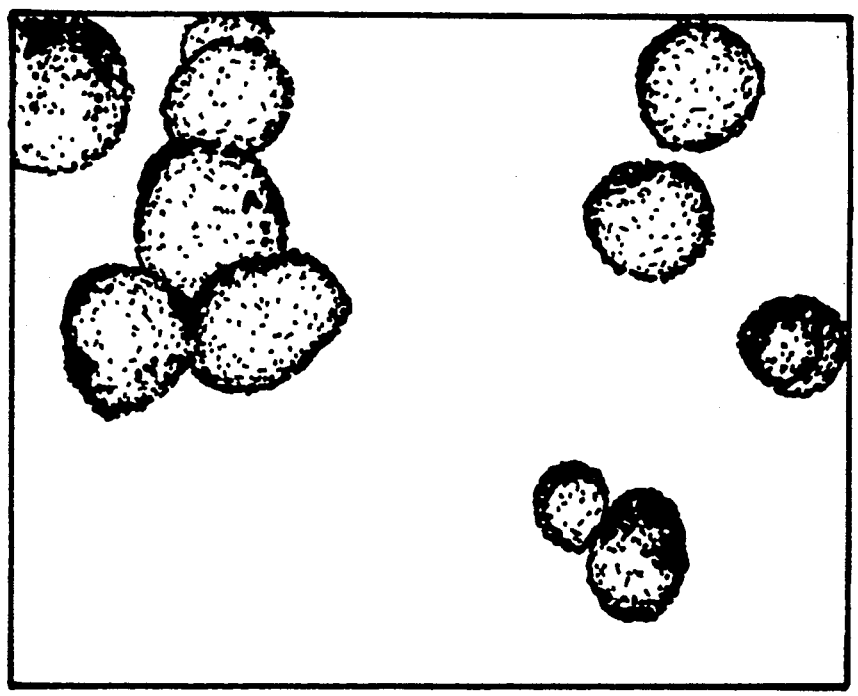
FIGS. 2A and 2B are scanning electron micrographs illustrating calcined baron-beta zeolites.
Figure 2B:
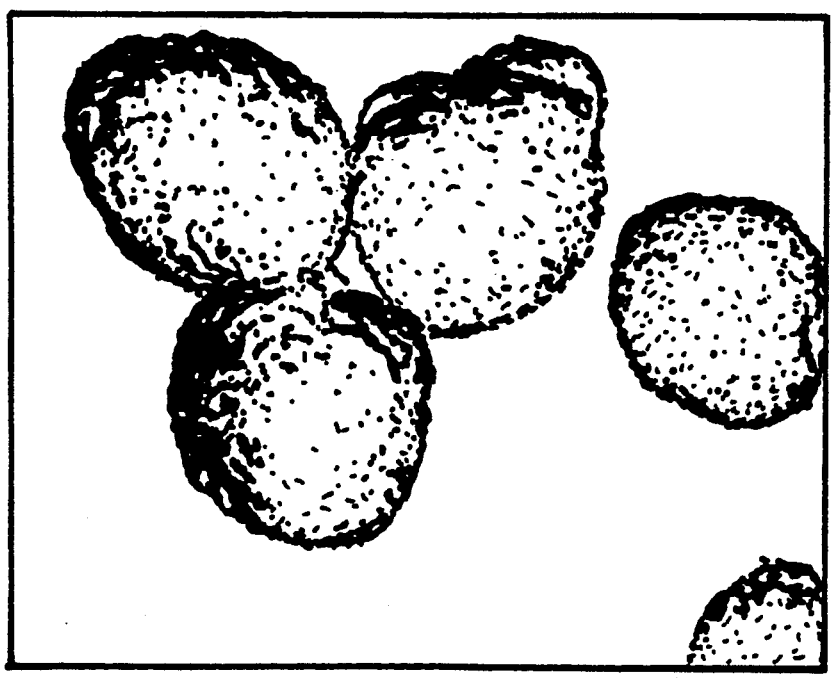

The solution had a pH of 13.0. The mixture was transferred to a teflon liner and sealed in a steel autoclave. The autoclave was kept in an oven at 165° C. for seven (7) days. After that, it was cooled and its contents were filtered. The recovered white crystalline material was washed with copious amounts of water and was dried at 110° C. for 16 hours. The dried sample was calcined at 592° C. under nitrogen for 4 hours and then under air for another 2 hours to remove the organic template. Table III, below, and FIG. 1 show the XRD of the uncalcined zeolite. Below, Table IV and FIG. 1 show the XRD of the calcined zeolite. FIGS. 2A and 2B show the SEM of the calcined zeolites.

TABLE III

| XFD Data of Synthesized [B]-Beta | |
|---|---|
| d space (A) | 100 I/Io |
| 11.34 | 37 |
| 11.19 | 38 |
| 4.08 | 10 |
| 3.90 | 100 |
| 3.47 | 5 |
| 3.26 | 13 |
| 2.98 | 10 |
| 2.89 | 3 |
| 2.64 | 3 |
| 2.04 | 7 |

TABLE IV

| XRD Data of Calcined [B]-Beta | |
|---|---|
| d space (A) | 100 I/Io |
| 11.47 | 100 |
| 11.25 | 68 |
| 6.54 | 10 |
| 6.01 | 12 |
| 5.87 | 5 |
| 4.07 | 9 |
| 3.90 | 55 |
| 3.47 | 6 |
| 3.27 | 9 |
| 2.98 | 5 |

EXAMPLE III

Conversion of 1-Butene to Isobutylene on Boron-Beta Zeolites

In this example, the procedure of Example II is used herein and the results are shown below in Table V.

TABLE V

| Catalyst | [B]-Beta, 1.28% B |
|---|---|
| Reaction conditions: | |
| 500 C., 1 atm, | |
| 4.7 WHSV, 1.64 N2/1-butene | |
| Time on stream, hr | 17 |
| * Conversion, C % | 18(30) |
| Selectivity, C % | |
| Isobutylene | 65(63) |
| C1 to C3 | 22(25) |
| C5+ | 10(9) |
| * Yield of isobutylene, carbon % | 11(19) |

* Average results shown first, results of 1st cut shown in parentheses.

Figure 3:
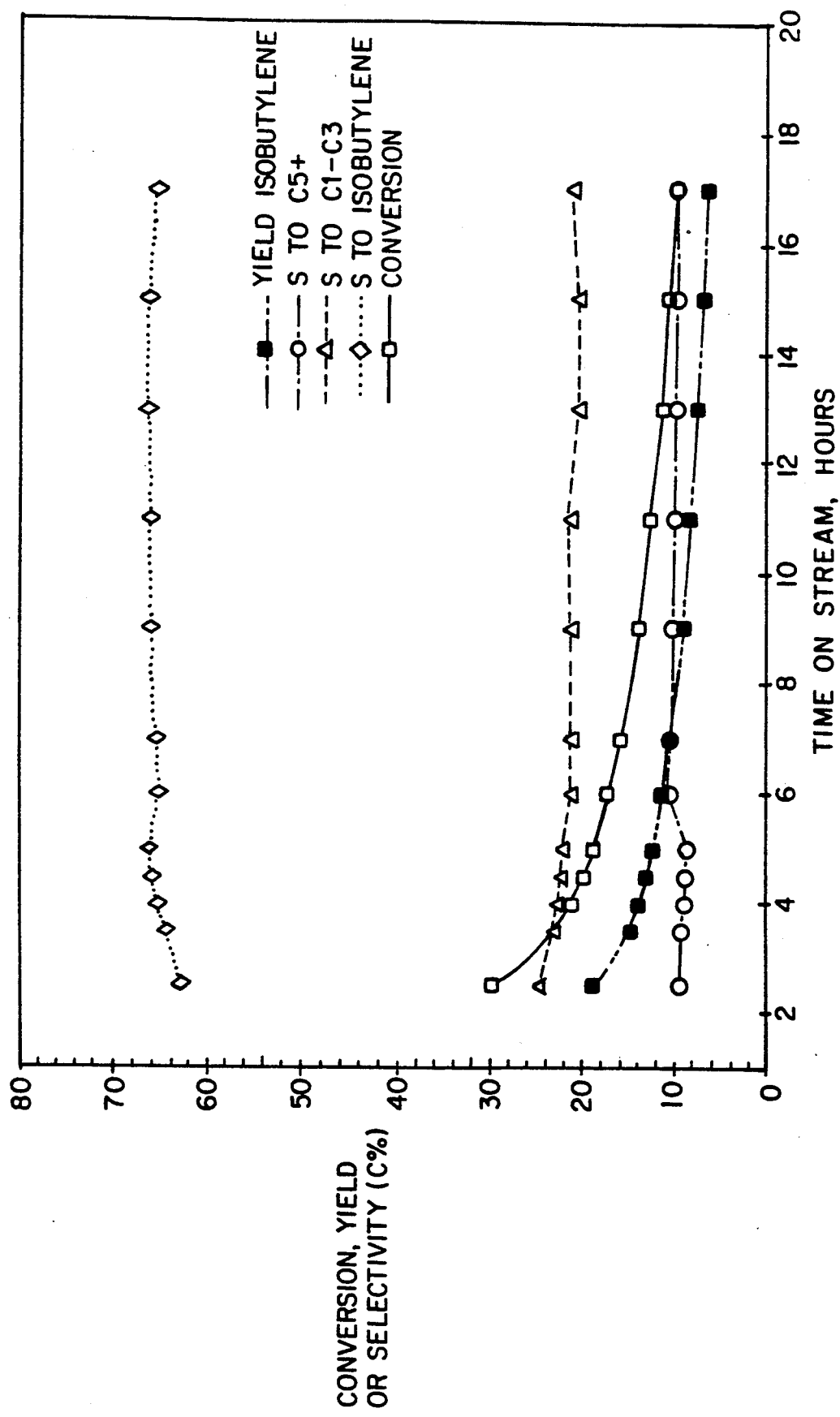
FIG. 3 is a graph of the Conversion or Selectivity (C %) vs. time on stream (hrs) of normal-alkene on boron-beta zeolite.
Figure 4:
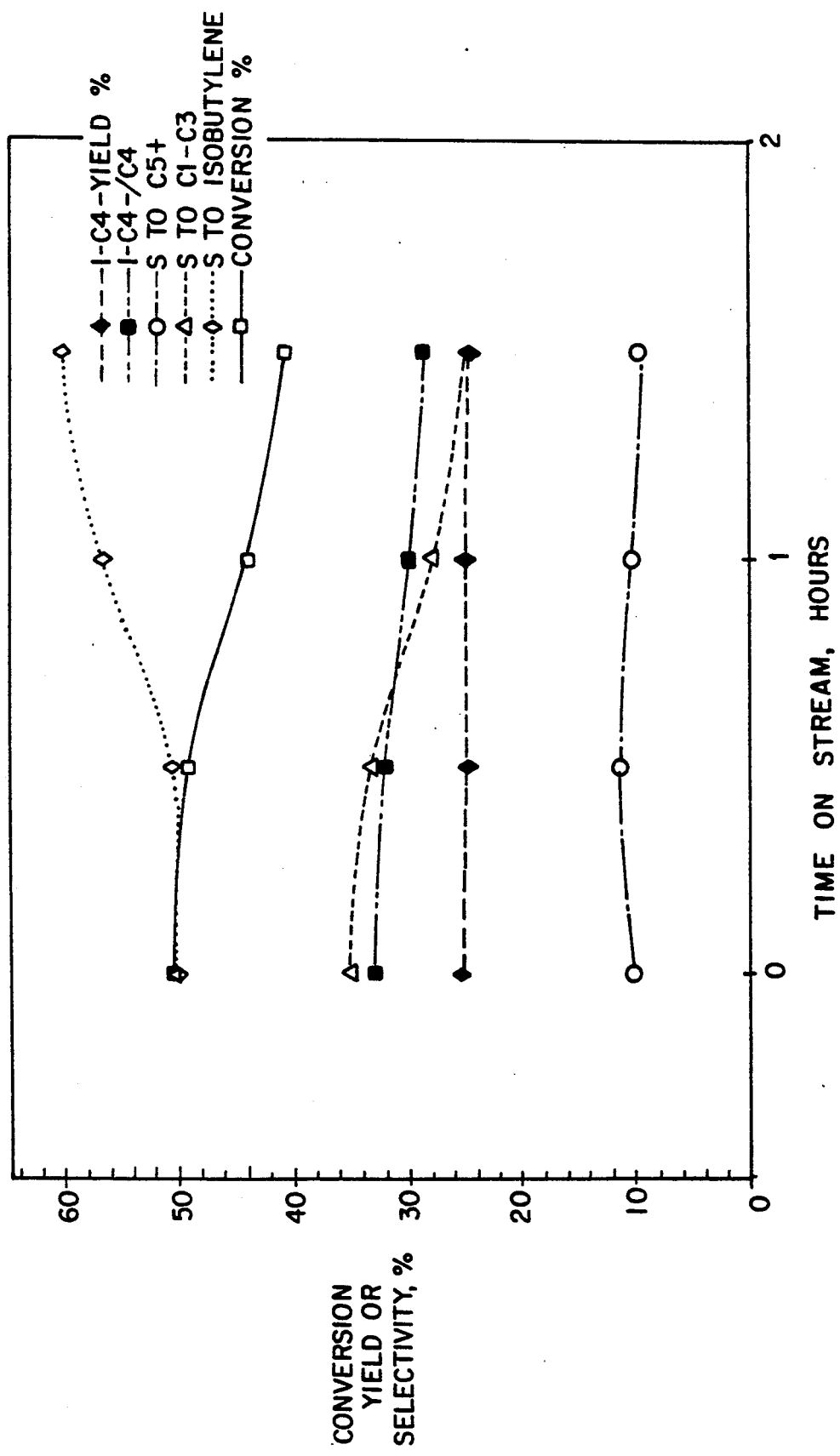
FIG. 4 is a graph of the Conversion or Selectivity (C %) vs. Time on Stream (hours) of C4 Raffinate on boron-beta zeolite.

Table III above, and FIG. 3 show results of the conversion of 1-butene to isobutylene on (B)-Beta zeolite. The run lasted 17 h. Average results are 18% conversion, 65% isobutylene selectivity, and 11% isobutylene yield. Results of the first cut are 30% conversion, 63% isobutylene selectivity, and 19% isobutylene yield.

EXAMPLE IV

Conversion of (C4) Raffinate to Enriched Isobutylene on Boron-Beta Zeolite Catalyst The same procedure as used in Example II was used in this Example. The results are presented below in Table VI.

TABLE VI

| Catalyst | [B]-Beta, 1.28% |
|---|---|
| Reaction conditions: | |
| 500° C., 1 atm, | |
| 4.7 WHSV, 1.64 $N_2$/1-butene | |
| Feed Composition: | |
| 33% i-butane, 15% n-butane, 17% 1-butene, | |
| 17% t-2-butene, 14% c-2 butene, 4% others. | |
| Time on stream, hr | 2 |
| * n-Butenes Conversion, C % | 46(50) |
| Selectivity, C % | |
| Isobutylene | 55(51) |
| C1 to C3 | 31(35) |
| C5+ | 11(10) |
| Yield of isobutylene, carbon % | 25(26) |

* Average results shown first, results of 1st cut shown in parentheses.

Table VI above shows results of a C4 raffinate feedstock on Boron-Beta Zeolite. The run lasted 2 hrs. The average results were 46% conversion, 55% isobutylene selectivity, and 26% isobutylene yield.

We claim:

1. A process for producing iso-olefins which comprises contacting a feedstock comprising at least one n-olefin with a catalyst comprising a boron-beta zeolite containing sufficient boron to provide sufficient acidity in said zeolite to catalyze the structural isomerization of said n-alkene to iso-alkenes.

2. The process of claim 1 wherein said beta-zeolite is characterized by topological structure of ZSM-11.

3. The process of claim 1 wherein said zeolite has a pore size of at least about 5 Angstroms and the pore structure is characterized by angular tunnels.

4. The process of claim 1 wherein said process was carried out between about 300° C. and about 650° C. and under a pressure between about 0.1 and about 100 atmospheres and a space velocity of between about 0.1 and about 40 (WHSV).

5. The process of claim 4, wherein said temperature is between 450° and 580° C., said pressure is between 0.1 and 40 atmospheres and said space velocity is between about 1 and about 20 (WHSV).

6. The process of claim 1 wherein said reaction is carried out in the presence of an inert diluent selected from the group consisting of nitrogen, steam and helium.

7. The process of claim 6 wherein the male ratio of said diluent to said n-alkene is between about 0.5 and about 10.0.

8. The process of claim 7 wherein said male ratio of said diluent to said n-alkene is between 0.5 and about 5.0.

9. The process of claim 1, wherein the boron content of said Beta zeolite is from about 0.1 to about 1.5 wt %.

10. The process of claim 1, wherein said beta-zeolite contains an inert binder selected from the group consisting of alumina, silica, alumina-silica, clays and combinations thereof.

11. The process of claim 1 wherein said feed consists of n-butenes and (C4) raffinates.

* * * * *